United States Patent [19]

Montgomery et al.

[11] Patent Number: 4,473,709

[45] Date of Patent: Sep. 25, 1984

[54] PYRETHROID INTERMEDIATES AND PROCESS

[75] Inventors: Ronald E. Montgomery, Middleport; Ernest L. Plummer, North Tonawanda, both of N.Y.; Anthony J. Martinez, Hamilton Square, N.J.

[73] Assignee: FMC Corporation, Philadelphia, Pa.

[21] Appl. No.: 168,870

[22] Filed: Jul. 14, 1980

[51] Int. Cl.³ ............................................. C07C 87/30
[52] U.S. Cl. ................................. 564/282; 564/337; 570/185; 570/191
[58] Field of Search ....................... 564/282, 305, 337; 568/631; 260/651; 570/185, 191

[56] References Cited

U.S. PATENT DOCUMENTS 4,214,004 7/1980 Plummer ........................... 564/282

OTHER PUBLICATIONS

A. T. Babayan et al., C. A., 84, 58806t (1976).
S. W. Kantor and C. R. Hauser, J. Am. Chem. Soc., 73, 4122 (1951).
C. Hauser et al., J. Org. Chem., 26, 4790 (1961).
The Merck Index, 9th Ed., ONR-83 (1976).
Organic Synthesis, Coll. vol. 4, 585 (1963).
Organic Reactions, 7, 198 (1953).
L. G. Humber, J. Med. Chem., 14, 982 (1971).
J. Braun and H. Engel, Ann., 436, 299 (1924); C. A., 18, 1831 (1924).
M. Sommelet, C. A., 17, 553 (1923).
Klein et al., Chem. Abst., vol. 66, #104758g (1967).
Archer, Chem. Abst., vol. 14, #141136p (1971).
Negero et al., Chem. Abst., vol. 63, #2937 (1965).

Primary Examiner—James H. Reamer
Attorney, Agent, or Firm—Robert M. Kennedy; H. Robinson Ertelt; Robert L. Andersen

[57] ABSTRACT

A novel N,N,N-trimethyl-[1,1'-biphenyl]-2-methanaminium compound is subjected to a rearrangement reaction to give a 3-dimethylaminomethyl-2-methyl-[1,1'-biphenyl] compound which is then converted to the corresponding 3-halomethyl-2-methyl-[1,1'-biphenyl] compound. The halomethyl compound is an intermediate for pyrethroid and related insecticides having the alcohol moiety derived from a 2-methyl-[1,1'-biphenyl]-3-methanol.

12 Claims, No Drawings

PYRETHROID INTERMEDIATES AND PROCESS

This invention relates to the preparation of intermediates for the production of pyrethroid or related insecticidal esters having the alcohol moiety derived from optionally substituted 2-methyl-[1,1'-biphenyl]-3-methanol.

In particular, the invention provides (i) a process for preparing an optionally substituted 3-halomethyl-2-methyl-[1,1'-biphenyl] compound directly from the corresponding 3-dimethylaminomethyl-2-methyl-[1,1'-biphenyl] compound, (ii) a process for preparing the 3-dimethylaminomethyl-2-methyl-[1,1'-biphenyl] compound from an N,N,N-trimethyl-[1,1'-biphenyl]-2-methanaminium compound, and (iii) a multi-step process for preparing the halomethyl compound from the methanaminium compound or a precursor compound of the methanaminium compound.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids and related compounds is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxybenzyl alcohol (see *Synthetic Pyrethroids*, ACS Symposium Series, No. 42, M. Elliott, Ed., American Chemical Society, Washington, D.C. 1977, Chapter 1).

A more recent discovery was that of the class of [1,1'-biphenyl]-3-methyl alcohols which form highly active insecticidal esters when chemically combined with 3-(2,2-dihaloethenyl)-2,2-dimethylcyclopropanecarboxylic acid (U.S. patent application Ser. No. 966,405, filed Dec. 4, 1978, allowed but not yet issued) and other acids commonly used in pyrethroid and related insecticides. One alcohol of this class of particular merit, which is disclosed in the U.S. patent application above, is 2-methyl-[1,1'-biphenyl]-3-methanol.

Commercial development of pyrethroids derived from 2-methyl-[1,1'-biphenyl]-3methanol has been hindered by the unavailability of a commercially feasible and efficient process for producing the alcohol or an appropriate derivative of it that could be converted directly into the final product pyrethroid.

In the method disclosed in the U.S. patent application above, 2-methyl-[1,1'-biphenyl]-3-methanol is produced in three steps starting with 2-methyl-3-nitrobenzyl alcohol, in about a 15% overall yield. The nitrobenzyl alcohol is converted in two steps to the corresponding iodobenzyl alcohol by reduction of the nitro group followed by replacement of the resulting amino group with an iodine atom in a Gattermann type reaction. The iodine atom is then replaced by a phenyl ring in a light initiated reaction with benzene. The method is illustrated by the following chemical equations:

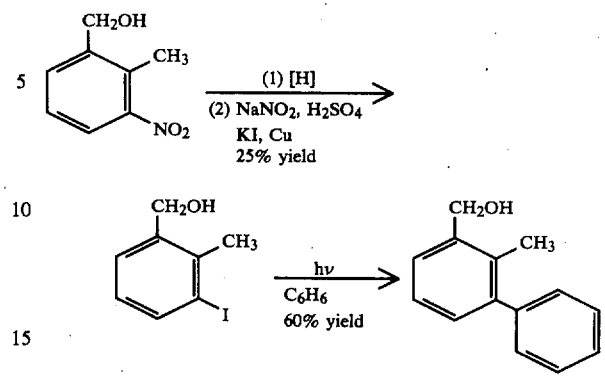

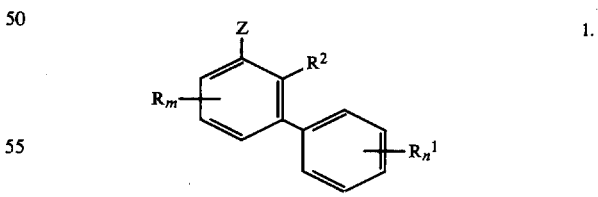

As a result of extensive studies, a general process has been discovered for preparing optionally substituted 3-halomethyl-2-methyl-[1,1'-biphenyl] in high yield from readily accessible starting materials as an intermediate for pyrethroid and related insecticides. The halomethyl intermediate can be converted directly into the desired insecticidal ester by reaction of the compound with a salt of the appropriate acid as exemplified in Example 4.

The following definitions are applicable throughout the specification and claims of this application except where a contrary meaning is clearly indicated:

The term "lower" as applied to an aliphatic group, as in "lower alkyl" or "lower alkoxy", means a straight or branched chain aliphatic group of 1 to 6 carbon atoms, preferably 1 to 4 carbon atoms. The term "halo" or "halogen" means fluorine, chlorine, bromine or iodine. The term "haloalkyl" means an alkyl group of 1 to 3 carbon atoms substituted with 1 or more halogen atoms and includes perhaloalkyl of 1 to 3 carbon atoms.

The present invention provides a process for preparing a halomethyl-methylbiphenyl compound 1(a) directly from the corresponding dimethylaminomethyl-methylbiphenyl compound 1(b), or indirectly from the aminium compound 1(c) by arrangement to 1(b) which is then converted to the desired product 1(a):

1.

$$\text{structure with } Z, R^2, R_m, R_n^1$$

(a) $Z = -CH_2X$, $R^2 = -CH_3$, $X = halo$
(b) $Z = -CH_2N(CH_3)_2$, $R^2 = -CH_3$
(c) $Z = -H$, $R^2 = -CH_2N^{\oplus}(CH_3)_3 Y^{\ominus}$ There are three process aspects and one composition of matter aspect to the present invention:

(A) One process aspect comprises a method for preparing a dimethylaminomethyl-methylbiphenyl compound of formula II by rearrangement of a methanaminium compound of formula I:

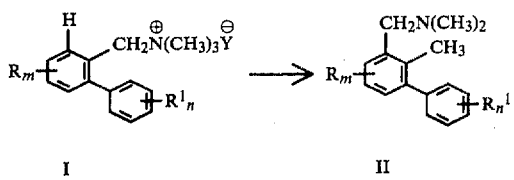

The substituents R and R[1] are the same or different and are selected from the group consisting of halogen, alkyl of 1 to 4 carbon atoms, fluoroalkyl of 1 carbon atom, alkoxy of 1 or 2 carbon atoms, and fluoroalkoxy of 1 to 2 carbon atoms; m is 0-3, preferably 0; n is 0-5, preferably 0; and Y is a chloride, bromide, iodide, or hydroxide ion, preferably an iodide ion. The rearrangement is similar to the Sommelet Rearrangement or the Sommelet-Hauser Rearrangement [*The Merck Index*, Martha Windholz, Ed., Merck & Co., Inc., 9th Edition, 1976, page ONR-83; and Organic Synthesis, Coll. Vol. 4, 585 (1963); both incorporated herein by reference], and is catalyzed by sulfuric acid, phosphorus pentoxide, or an alkali metal amide such as sodium or potassium amide. The use of an alkali metal amide, particularly sodium amide, is preferred. When sodium amide is used, it is advantageous to conduct the rearrangement in the presence of liquified ammonia, and to prepare the sodium amide in situ by addition of metallic sodium, in small portions, to the liquified ammonium in the reaction vessel. Preparation of the sodium amide by this method is generally facilitated by adding a small amount of ferric nitrate to the liquified ammonia.

In a preferred embodiment wherein m and n are each 0, and Y is an iodide ion, and the rearrangement is conducted in the presence of sodium amide, prepared in situ, in liquified ammonia, the dimethylaminoethyl-methylbiphenyl compound of formula II is obtained in about an 80% yield. This reaction is described more fully in Example 2 below.

(B) In a second process aspect of the invention, a dimethylaminomethyl-methylbiphenyl compound of formula II is converted to the corresponding halomethyl compound of formula III, wherein R, R[1], m, and n are as defined above in (A), and X is a halogen, such as a bromine or chlorine atom, preferably a chlorine atom.

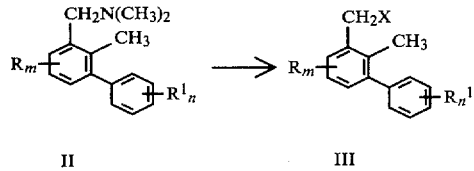

In this aspect of the invention, the dimethylaminoethyl-methylbiphenyl compound, wherein m and n are preferably 0, is subjected to a von Braun type degradation to give the corresponding halomethyl compound.

The bromomethyl compound (III, X=—Br) is prepared by the reaction of the compound of formula II with cyanogen bromide. This reaction is analogous to the normal von Braun degradation, and proceeds under the conditions described for that reaction in *Organic Reactions*, 7, 198 (1953), incorporated herein by reference. The reaction is usually conducted at a temperature in the range of about 0° C. to the boiling point of cyanogen bromide, about 60° C., and is preferably conducted at or about the temperature of reflux. If the reaction is to be conducted at a temperature higher than 60° C., a pressure reactor should be used. An inert solvent such as benzene, toluene, or xylene is generally used, except when the reaction is performed under pressure.

The chloromethyl derivative (III, X=—Cl) is prepared by contacting the dimethylaminomethyl-methylbiphenyl compound, II, with either methyl or ethyl chloroformate, preferably ethyl chloroformate, at an elevated temperature generally in the range of about 50° C. to the boiling point of the chloroformate used. The reaction is conveniently conducted in the presence of an inert solvent, for example, an aromatic hydrocarbon such as benzene, toluene, or xylene. This reaction is similar to Gadamer-Knoch modification of the von Braun degradation as described by L. G. Humber in *J. Med. Chem.*, 14, 982 (1971), incorporated herein by reference. The conversion proceeds with relative ease and in a very high yield, and for this reason is preferred to the normal von Braun type reaction discussed above. This aspect of the invention is exemplified in Example 3 below wherein the chloromethyl derivative was obtained in quantitative yield from the compound of formula II wherein m and n are 0. The reaction was conducted in the presence of ethyl chloroformate and toluene at about 80° C.

(C) The third process aspect of the invention comprises a method for preparing the halomethyl-methylbiphenyl compound of formula III in two steps from the methanaminium compound of formula I, or in three or more steps from a compound (formula IV, V, VI, or VII below) which can be converted into the methanaminium compound. The individual steps of the two-step process are those described above for the first two process aspects of the invention. The number of additional steps will depend upon the choice of starting material and the number of steps required to convert it to the methanaminium compound.

Various methods may be used to prepare the methanaminium compound. In the method of the present invention, illustrated in the chemical equations below, an appropriate 2-biphenylcarboxylic acid, formula IV, is converted into the corresponding dimethylamide VI by treatment of the acid halide derivative V with dimethylamine or, preferably, dimethylformamide. The dimethylamide compound is then reduced, advantageously by treatment with lithium aluminum hydride, to give the corresponding dimethylamine derivative VII, which is converted into the methanaminium halide I (Y is Cl, Br, or I) by treatment with the appropriate methyl halide. The methanaminium hydroxide (Y is OH) may be prepared by treating the corresponding methanaminium halide with silver oxide in water.

In the chemical equations below R, R[1], m and n are as defined above, and Y is a chloride, bromide, or iodide ion. This series of reactions for the compounds wherein m and n are 0, and Y is an iodide ion is described in greater detail in Example 1.

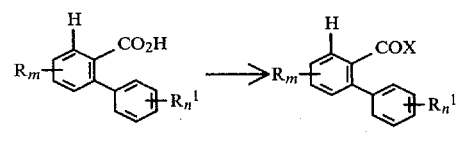

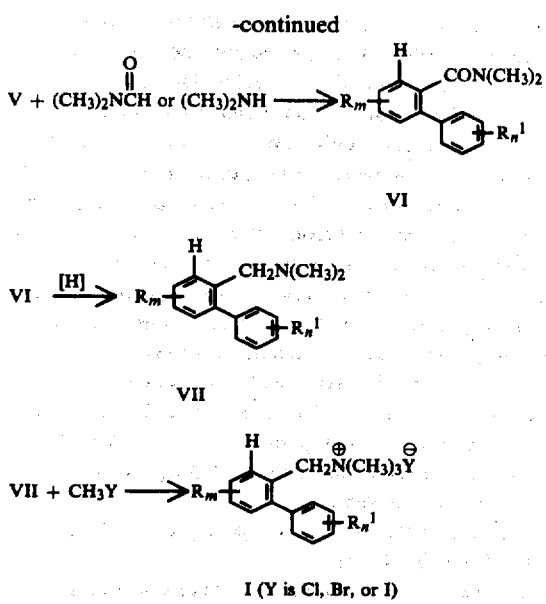

The composition of matter aspect of the present invention relates to the methanaminium compound of formula I wherein R, $R^1$, m, and n are as defined above, and Y is a chloride, bromide, iodide, or hydroxide ion, preferably an iodide ion. In a preferred embodiment m and n are each 0. The critical feature of this compound is the placement of the methanaminium group at C-2 of the first phenyl ring, adjacent to the second phenyl ring, since it results in the methyl group being situated at C-2 between the methylene carbon at C-3 and the phenyl ring at C-1 in the 3-halomethyl-2-methyl-[1,1'-biphenyl] product of the present process and pyrethroid insecticides derived therefrom. Such pyrethroid insecticides show unexpectedly high insecticidal activity which is attributed to this particular placement of groups.

The Examples which follow illustrate the process of the present invention, the preparation of starting materials used therein, and the utility of the products thereof as intermediates for pyrethroid and related insecticides, in accordance with the general methods described above. In the Examples, temperatures are in degrees Celsius and pressures are in mm Hg.

EXAMPLE 1

PREPARATION OF N,N,N-TRIMETHYL-[1,1'-BIPHENYL]-2-METHANAMINIUM IODIDE

Step A. [1,1'-Biphenyl]-2-Carbonyl Chloride

Under a dry nitrogen atmosphere 10 g (0.05 mole) of 2-biphenylcarboxylic acid was dissolved with stirring in 116 ml of dry toluene. Pyridine, 4.2 g (0.054 mole), was then added to the reaction mixture followed by 6.4 g (0.054 mole) of thionyl chloride. The reaction mixture was stirred at room temperature for two hours, then filtered to remove a white precipitate. The toluene was removed from the filtrate under reduced pressure to give [1,1'-biphenyl]-2-carbonyl chloride as a liquid residue, which was used without purification in Step B below.

Step B. N,N-Dimethyl-[1,1'-Biphenyl]-2-Carboxamide

This compound was prepared by a method similar to that described by C. M. Coppinger, J. Am. Chem. Soc., 76, 1372 (1954), for N,N-dimethylbenzamide.

Under a dry nitrogen atmosphere, 7.3 g (0.1 mole) of dimethylformamide was added with stirring to the [1,1'-biphenyl]-2-carbonyl chloride residue from Step A above. The reaction mixture was heated at reflux temperature for 3.5 hours, then cooled to room temperature where it was allowed to stand for 16 hours.

A white crystalline precipitate which had formed in the reaction mixture was collected by filtration. The precipitate was dissolved in ethanol and combined with the filtrate. The ethanol was removed under reduced pressure and the excess dimethylformamide was removed by short path distillation at 120° C./5 mm to give a semi-solid residue. The residue was dissolved in methylene chloride and washed with three 10 ml portions of a 10% aqueous solution of sodium hydroxide. The organic phase was dried with anhydrous sodium sulfate and filtered. The solvent was removed from the filtrate to give 6.1 g (61% yield from biphenylcarboxylic acid) of N,N-dimethyl-[1,1'-biphenyl]-2-carboxamide as a dark oil.

The nmr and infra red spectra were consistent with the proposed structure.

Step C. N,N-Dimethyl-[1,1'-Biphenyl]-2-Methanamine

Under a dry nitrogen atmosphere, 6.1 g (0.027 mole) of N,N-dimethyl-[1,1'-biphenyl]-2-carboxamide was dissolved with stirring in 250 ml of dry 1,2-dimethoxyethane. To this solution was added portionwise 1.3 g (0.034 mole) of lithium aluminum hydride. Upon complete addition, the reaction mixture was heated at reflux temperature for 18 hours. The reaction mixture was then cooled to room temperature, and 1.22 ml (0.068 mole) of water was added dropwise. The reaction mixture was filtered, and the filtrate concentrated under reduced pressure to give 6.1 g (100% yield) of N,N-dimethyl-[1,1'-biphenyl]-2-methanamine as a yellow liquid.

The nmr and infra red spectra were consistent with the proposed structure.

Step D. N,N,N-Trimethyl-[1,1'-Biphenyl]-2-Methanaminium Iodide

Under a dry nitrogen atmosphere, 6.1 g (0.027 mole) of N,N-dimethyl-[1,1'-biphenyl]-2-methanamine was dissolved with stirring in 6.4 ml of anhydrous ethanol. To this solution 5.1 g (0.036 mole) of methyl iodide was added slowly. After complete addition, the reaction mixture was heated at reflux temperature for 45 minutes, then cooled. Diethyl ether was added until the mixture was cloudy, then the whole was placed in a freezer for 16 hours. An oil which had formed in the mixture was separated then dissolved in ethanol, and the solution was concentrated under reduced pressure to give 10.0 g (100% yield) of N,N,N-trimethyl-[1,1'-biphenyl]-2-methanaminium iodide as a brittle yellow foam.

The nmr spectrum was consistent with the proposed structure.

EXAMPLE 2

PREPARATION OF N,N,2-TRIMETHYL-[1,1'-BIPHENYL]-3-METHANAMINE

A small amount of metallic sodium, about 0.1 g, was added with stirring at −40° C. to −60° C. to a reaction flask containing about 22 ml of liquified ammonia to give a persistent dark blue color. Ferric Nitrate, 0.014 g, was added, causing the color of the reaction mixture to change from blue to gray. Additional metallic sodium, 0.74 g total (0.032 mole), was added during 15 minutes, restoring the blue color. Stirring was continued until the blue color faded to a gray-black color, about 10 minutes, then 10.0 g (0.027 mole) of N,N,N-trimethyl-[1,1'-biphenyl]-2-methanaminium iodide was added with stirring during 15 minutes. Ammonia was added to bring the volume to its original level, and the reaction mixture was stirred for 75 minutes. Ammonium chloride, 0.72 g (0.0135 mole), was added slowly, then 15 ml water was added and the reaction mixture was allowed to stand overnight.

The reaction mixture was diluted with water and extracted with three 25 ml portions of diethyl ether. The extracts were combined and washed twice with an aqueous saturated sodium chloride solution. The organic layer was dried with anhydrous potassium carbonate and filtered. The solvent was removed from the filtrate under reduced pressure to give 2.1 g (80.4% yield) of N,N,2-trimethyl-[1,1'-biphenyl]-3-methanamine.

The nmr and infra red spectra were consistent with the proposed structure.

EXAMPLE 3

PREPARATION OF 3-CHLOROMETHYL-2-METHYL-[1,1'-BIPHENYL]

Under a dry nitrogen atmosphere, 0.5 g (0.0022 mole) of N,N,2-trimethyl-[1,1'-biphenyl]-3-methanamine was dissolved in 5.5 ml of dry toluene with stirring and the solution was heated to 80° C. A solution of 0.36 g (0.0033 mole) of ethyl chloroformate in 1.1 ml of dry toluene was added dropwise during 5 minutes. The reaction mixture was stirred for 3.3 hours at 80° C., then cooled to room temperature and filtered. The solvent was removed from the filtrate under reduced pressure to give 0.5 g (100% yield) of 3-chloromethyl-2-methyl-[1,1'-biphenyl] as a light orange oil.

The $^1$H and $^{13}$C nmr spectra and infra red spectrum were consistent with the proposed structure.

EXAMPLE 4

PREPARATION OF [2-METHYL-(1,1'-BIPHENYL)-3-YL]METHYL CIS-3-(2-CHLORO-3,3,3-TRIFLUORO-PROPENYL)-2,2-DIMETHYLCYCLO-PROPANECARBOXYLATE

To a solution of 0.62 g (0.011 mole) of potassium hydroxide in 3.65 ml distilled water was added, with stirring, 1.8 g (0.0074 mole) of cis-3-(2-chloro-3,3,3-trifluoropropenyl)-2,2-dimethylcyclopropanecarboxylic acid and 14.6 ml of heptane. The reaction mixture was heated at reflux temperature, and the water was collected in a Dean-Stark trap. The anhydrous reaction mixture was then cooled, and 1.5 g (0.0069 mole) of 3-chloromethyl-2-methyl-[1,1'-biphenyl] and 14.6 ml of acetonitrile were added. The reaction mixture was stirred and heated at reflux temperature for 16 hours, then cooled and diluted with water. Diethyl ether was added and the two phases were separated. The aqueous phase was washed with heptane, then with diethyl ether. The organic phase and washings were combined, dried with anhydrous sodium sulfate and filtered. The solvents were removed from the filtrate under reduced pressure to give a yellow oil which was dissolved in methylene chloride and subjected to preparative liquid chromatography. A mixture of hexane and methylene chloride (2:1) was used as eluant. Appropriate fractions, as determined by thin layer and gas liquid phase chromatography, were combined to give 1.6 g of [2-methyl(1,1'-biphenyl)-3-yl]methyl cis-3-(2-chloro-3,3,3-trifluoropropenyl)-2,2-dimethylcyclopropanecarboxylate as a clear, colorless oil.

Analysis calculated for $C_{23}H_{22}F_3O_2$: C 65.32; H 5.24; Found: C 65.07; H 5.41.

The nmr and infra red spectra were consistent with the proposed structure.

We claim:

1. A compound of the formula

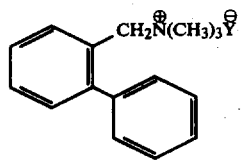

wherein Y is a chloride, bromide, iodide, or hydroxide ion.

2. The compound of claim 1 wherein Y is an iodide ion.

3. A process for preparing a dimethylaminomethyl-methylbiphenyl compound of the formula

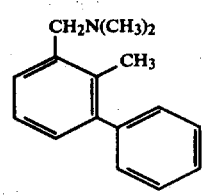

which comprises treating a methanaminium compound of the formula

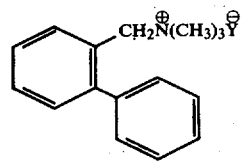

wherein Y is a chloride, bromide, iodide, or hydroxide ion with an alkali metal amide in liquid ammonia.

4. A process for preparing a halomethyl-methyl-biphenyl compound of the formula

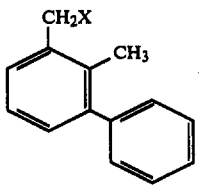

wherein X is a chlorine or bromine atom which comprises the steps of (a) treating a methanaminium compound of the formula

wherein Y is a chloride, bromide, iodide, or hydroxide ion with an alkali metal amide in liquid ammonia to give a dimethylaminomethyl-methylbiphenyl compound of the formula

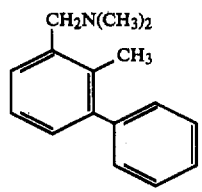

and then, (b) treating the dimethylaminomethylmethylbiphenyl compound with methyl chloroformate or ethyl chloroformate to give the compound wherein X is a chlorine atom, or with cyanogen bromide to give the compound wherein X is a bromine atom.

5. The process of claim 3 wherein the alkali metal amide is sodium amide.

6. The process of claim 5 wherein Y is an iodide ion.

7. The process of claim 4 wherein the alkali metal amide is sodium amide.

8. The process of claim 15 wherein Y is an iodide ion.

9. The process of claim 4 wherein X is a chlorine atom and the dimethylaminomethyl-methylbiphenyl compound is converted into the chloromethyl-methylbiphenyl compound by treatment with methyl or ethyl chloroformate at a temperature in the range of about 50° C. to the boiling point of the chloroformate used.

10. The process of claim 9 wherein the conversion is effected with ethyl chloroformate.

11. The process of claim 10 wherein the conversion is conducted in an inert solvent at a temperature in the range of about 70° C. to 90° C.

12. The process of claim 4 wherein X is a bromine atom and the dimethylaminomethyl-methylbiphenyl compound is converted to the bromomethyl-methylbiphenyl compound by treatment with cyanogen bromide at a temperature in the range of about 0° C. to 60° C.

* * * * *